United States Patent
Hirokawa et al.

(10) Patent No.: US 8,189,736 B2
(45) Date of Patent: May 29, 2012

(54) X-RAY CT APPARATUS

(75) Inventors: Koichi Hirokawa, Tokyo (JP); Taiga Goto, Tokyo (JP); Takayuki Kadomura, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 354 days.

(21) Appl. No.: 12/671,872

(22) PCT Filed: Aug. 6, 2008

(86) PCT No.: PCT/JP2008/064084
§ 371 (c)(1), (2), (4) Date: Feb. 2, 2010

(87) PCT Pub. No.: WO2009/020136
PCT Pub. Date: Feb. 12, 2009

(65) Prior Publication Data
US 2010/0232566 A1    Sep. 16, 2010

(30) Foreign Application Priority Data
Aug. 6, 2007 (JP) ................................ 2007-203723

(51) Int. Cl.
*A61B 6/00* (2006.01)
(52) U.S. Cl. ............................................. 378/5; 378/15
(58) Field of Classification Search .................. 378/4, 5, 378/15, 16, 101, 109–112, 114–116
See application file for complete search history.

(56) References Cited

U.S. PATENT DOCUMENTS
7,711,082 B2 * 5/2010 Fujimoto et al. ................ 378/16
2006/0109951 A1 5/2006 Popescu FOREIGN PATENT DOCUMENTS
JP 2006-122679 5/2006
JP 2006-271437 10/2006
JP 2008-154669 7/2008

* cited by examiner

Primary Examiner — Jurie Yun
(74) Attorney, Agent, or Firm — Cooper & Dunham LLP

(57) ABSTRACT

Provided is an X-ray CT apparatus which can perform CT scan of multi-energy scanning at a high speed and can obtain an image having an excellent substance distinguishing ability. The X-ray CT apparatus includes: means to continuously perform a first CT scanning using a first X-ray energy and a second CT scanning using a second X-ray energy without interrupting CT scan; means to transit the X-ray energy emitted from the X-ray during a transition period TR including an end of the first CT scanning and a beginning of the second CT scanning from the first X-ray energy to the second X-ray energy; and means to compensate the scan data in the transition period by the opposing data in the residual scan period so as to reconstruct an image.

9 Claims, 9 Drawing Sheets

(a)

(b)

X-RAY CT APPARATUS

TECHNICAL FIELD

The present invention is related to an X-ray CT apparatus, particularly to the X-ray CT apparatus provided with a multi-energy scanning function.

BACKGROUND ART

In recent years, the X-ray CT apparatus provided with multi-energy scanning function has been developed capable of acquiring CT images by different effective photon energies by using a plurality of different tube voltages upon scanning the same tomographic plane or providing discriminating function of X-ray photon energies to an X-ray detector.

The advantage of the multi-energy scanning is that it is possible to distinguish the subjects, for example a bone and a contrast-filled blood vessel having proper concentration that are difficult to distinguish by a single effective energy since the CT values of the subjects are the same, by using different effective energies which makes the subjects have different CT values.

The configuration methods for the X-ray CT apparatus comprising the above-mentioned multi-energy scanning function will be described below and they are commonly-known in the Patent Documents to be listed below and in the meeting held by Radiological Society of North America in 2006.

(1) First Method

The X-ray CT apparatus is mounted with a plurality of pairs of an X-ray tube and an X-ray detector, so as to execute measurement by different tube voltages in each pair (hereinafter referred to as the multi-source/multilayered-detector method). This method is disclosed in Patent Document 1.

(2) Second Method

The X-ray detector is multilayered with respect to the transmitting direction of an X-ray so as to acquire the measurement data by different effective energies for each layer of the detector (hereinafter referred to as the multilayered detector method). This multilayered detector method is capable of multi-energy scanning without scanning by different tube voltages, and is disclosed in Patent Document 2.

(3) Third Method

This method comprises a pair of X-ray tubes and a non-multilayered X-ray detector so as to execute plural times of scanning with different tube voltages with respect to the same tomographic plane. The representative method irradiates an X-ray during ⅔ rotation in the first rotation after start of scanning, stops X-ray irradiation during the next ⅓ rotation so as to set the tube voltage different from the first scanning for the next scanning, and executes the next ⅔ rotation of scanning with the tube voltage set to be different from the first scanning (hereinafter referred to as the multi-half scanning method).

This method is disclosed in Non-patent Document 1 from the meeting Radiological Society of North America held in 2006.

Patent Document 1: Japanese Patent No. 3405760
Patent Document 2: JP-A-2001-174564
Non-patent Document 1: A. Ueno et al. "Evaluation and Assessment of Material Decomposition between Bone/Calcification and Iodine for CT Angiography Using 40 mm Coverage Volumetric CT with Novel High-Speed Pulsed Dual Energy Scanning", Radiological Society of North America; Scientific Assembly and Annual Meeting Program 2006, pp 962, LL-VI2525

DISCLOSURE OF THE INVENTION

Problems to be Solved

However, the above-described multi-energy scanning methods have the problems below in economical efficiency and performance.

(1) Multi-Source/Multi-Layered Detector Method

Since a plurality of X-ray sources and X-ray detectors need to be mounted in a scanner rotation unit, the apparatus becomes large in size and expensive. Also, upon clinical usage, characteristic of a plurality of X-ray generating systems and X-ray detecting systems need to be matched.

Therefore, it is assumed that it requires a considerable period of time for matching the characteristics of a plurality of X-ray generating systems and X-ray detecting systems, and that means for compensating the difference in characteristic errors, etc. is required.

(2) Multi-Layered Detector Method

Compared to the multi-energy scanning which scans with different tube voltages (the voltage to be applied between the anode and the cathode of an X-ray tube), the difference among the effective energies of the X-ray energy detected in the respective layers of a detector is small, thus substance distinguishing ability needs to be improved comparing the other above-described multi-energy scanning methods.

Also, since multi-layer X-ray detectors are used, the apparatus becomes expensive though not as much as the multi-source/multilayered-detector method.

(3) Multi-Half Scanning Method

In the present scanning method, since the half-scan reconstruction method is likely to be applied as the image reconstruction method with respect to the data measured at ⅔ rotation, it is assumed that the greater image noise will be generated compared to the full-scan (there is no interruption of X-ray irradiation during one rotation) image reconstruction method.

Also, since there is no opposing data (measurement data at the time that the X-ray tube is at 180 degrees opposite position) in the half-scan method, lack of the off-set detector effect (improves spatial resolution and reduces streak artifacts) remains a problem.

Further, since this method requires ⅓ rotation of interruption time in X-ray irradiation, it is hard to say that the advantage of high-speed by applying the half-scan method can be fully received.

As mentioned above, a significant problem still remains in each of the conventional multi-energy scanning method. The objective of the present invention is to provide an X-ray CT apparatus considering the above-mentioned problems, which comprises the multi-energy scanning function capable of acquiring images having an excellent substance distinguishing ability at a high speed that executes plural times of scanning for scanning the same portion.

Means to Solve the Problem

In order to achieve the above-mentioned objective, the X-ray CT apparatus of the present invention includes:

a pair of an X-ray tube and an X-ray detector configured to irradiate an X-ray to an object to be examined and to detect the X-ray transmitted through the object;

scanner rotation means mounted with the pair of the X-ray tube and the X-ray detector configured to rotate them around the object;

multi-energy scanning planning means configured to CT scan the object at the same slice position with the X-rays having different X-ray energies; and X-ray control means configured to control the irradiation of the X-rays having the different X-ray energies from the X-ray tube, is characterized in further comprising:

means configured to continually perform a first CT scanning using a first X-ray energy and a second CT scanning using a second X-ray energy without interrupting CT scan;

means configured to transit the X-ray energy emitted from the X-ray tube during a transition period including an end of the first scanning and a beginning of the second CT scanning, from the first X-ray energy to the second X-ray energy; and means configured to compensate the scan data in the transition period using the opposing data in the residual scan period so as to reconstruct an image.

The above-described X-ray CT apparatus of the present invention performs multi-energy CT scanning at a high speed by continuously performing a first CT scanning using a first X-ray energy and a second CT scanning using a second X-ray energy without interruption. For switching from the first X-ray energy of the first CT scanning to the second X-ray energy of the second CT scanning, the period including an end of the first CT scanning and a beginning of the second CT scanning is set as a transition period for switching the X-ray conditions. During this transition period, the X-ray condition (tube voltage, tube current) drastically changes since the transition period accounts for a very small proportion of the scan time. For this reason, negative effects can be expected when the scan data acquired during this transition period is used for image reconstruction along with the scan data acquired in the other period.

Given this factor, in order to minimize the negative effect, the scan data during the transition period is to be compensated by the scan data of the residual period. More specifically, the scan data in the transition period is to be compensated by reducing the weight of the scan data in the transition period so as to reduce the influence of the scan data thereof on image reconstruction of the scan data during the transition period, and increasing the weight of the opposing data thereof for the reduced portion.

While the opposing data of the scan data in the transition period is necessary for executing the above-described data compensation in the present invention, if the opposing data in the transition period can be acquired during the residual scan period, the first CT scan and the second CT scan may be performed as the half scan in less than one rotation other than the full scan of one rotation.

Effect of the Invention

As mentioned above, in accordance with the present invention, it is possible to perform multi-energy scanning which is inexpensive and has sufficient difference in X-ray effective energies compared to the multi-radiation source/multilayered-detector method or multi-layer detector method since a plurality of different tube voltages can be switched without interruption using a pair of an X-ray tube and a detector, to provide an X-ray CT apparatus comprising a multi-energy scanning function capable of acquiring high quality images with reduced image noise or streak artifacts which has a greater matter distinguishing ability than the half scan method since the scan in the respective tube voltages are full scan.

BRIEF DESCRIPTION OF THE DIAGRAMS

DESCRIPTION OF NUMERAL REFERENCES

1: scanner gantry, 2: table, 3: console, 4: top board, 5: display device, 6: operation device, 7: X-ray control device, 8: X-ray tube, 11: non-multi X-ray detector, 13: scanner rotor plate, 17: object, 19: multi-energy scanning system controller, 20: table controller, 21: table vertical movement device, 22: top-board moving device, 23: image reconstruction device, 24: storage device, 25: scan planning device for multi-energy scanning, 27: tube voltage/tube current detector, k: scan counter, P: number of tube voltage kinds

BEST MODE FOR CARRYING OUT THE INVENTION

First embodiment of the X-ray CT apparatus related to the present invention will be described below in detail referring to the attached diagrams.

While the present invention is applicable to any of the single-slice type and multi-slice type, the case that is applied to the multi-slice type X-ray CT apparatus will be described here.

Figure 1:
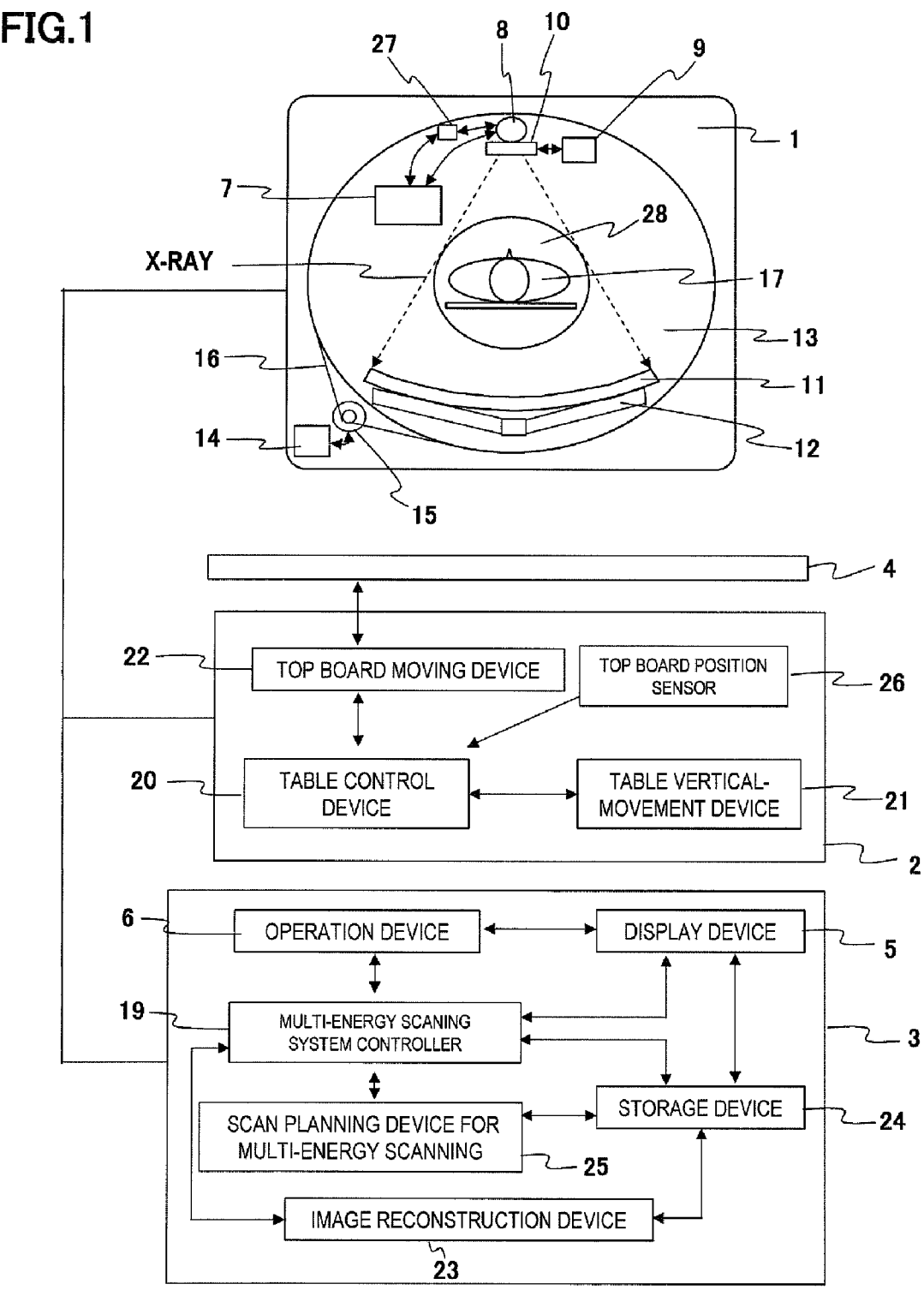
FIG. 1 is a general block diagram of the X-ray CT apparatus to which the present invention is applied.
Figure 2:
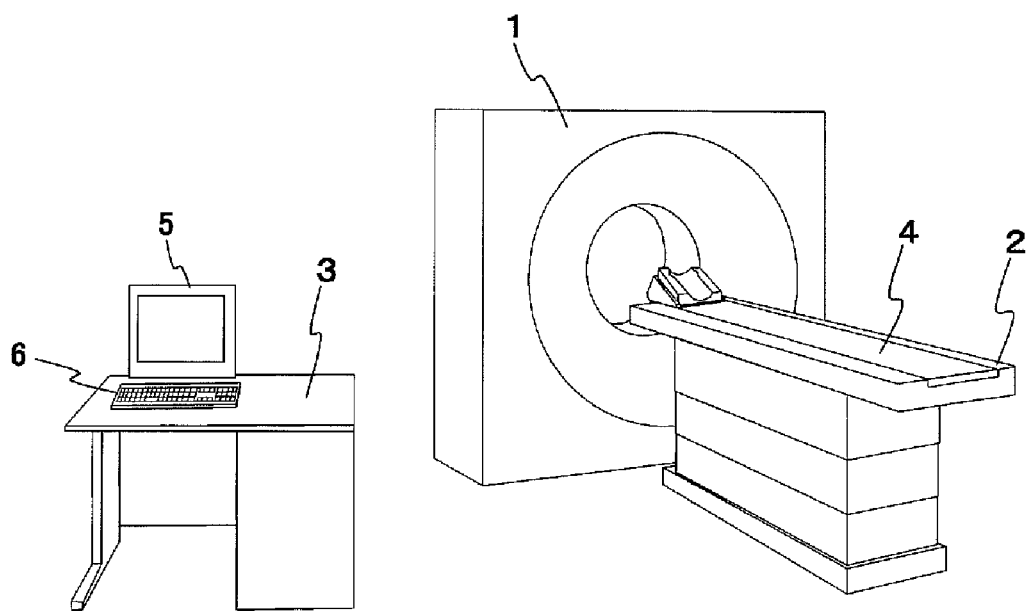
FIG. 2 is a general overview of the X-ray CT apparatus to which the present invention is applied.

FIG. 2 shows a general overview of the X-ray CT apparatus to which the present invention is applied, and FIG. 1 shows the general configuration thereof.

The X-CT apparatus shown in FIG. 2 irradiates X-rays to an object to be examined and collects data of the X-rays transmitted through the object so as to acquire tomographic images of the collected X-ray data by performing reconstruction calculation. It is configured by scanner gantry 1 configured to irradiate X-rays to the object and collects the X-ray data transmitted through the object, table 2 comprising movable top board 4 on which the object is to be placed, and console 3 comprising operation device 6 and display device 5, etc. configured to execute settings of various operations as well as to reconstruct and display X-ray tomographic images based on the collected X-ray data.

The scanner gantry 1 is configured as shown in FIG. 1, and comprises X-ray tube 8 controlled by X-ray controller 7 so as to generate X-rays and X-ray detector 11. The X-rays emitted from X-ray tube 8 are made into, for example, pyramidal X-ray beams, i.e. cone-beam X-rays by collimator 10 under control of collimator controller 9, and irradiated to object 17.

The X-rays transmitted through object 17 are detected by non-multi X-ray detector 11 (a pair of an X-ray tube and a non-multi X-ray detector).

Figure 3:
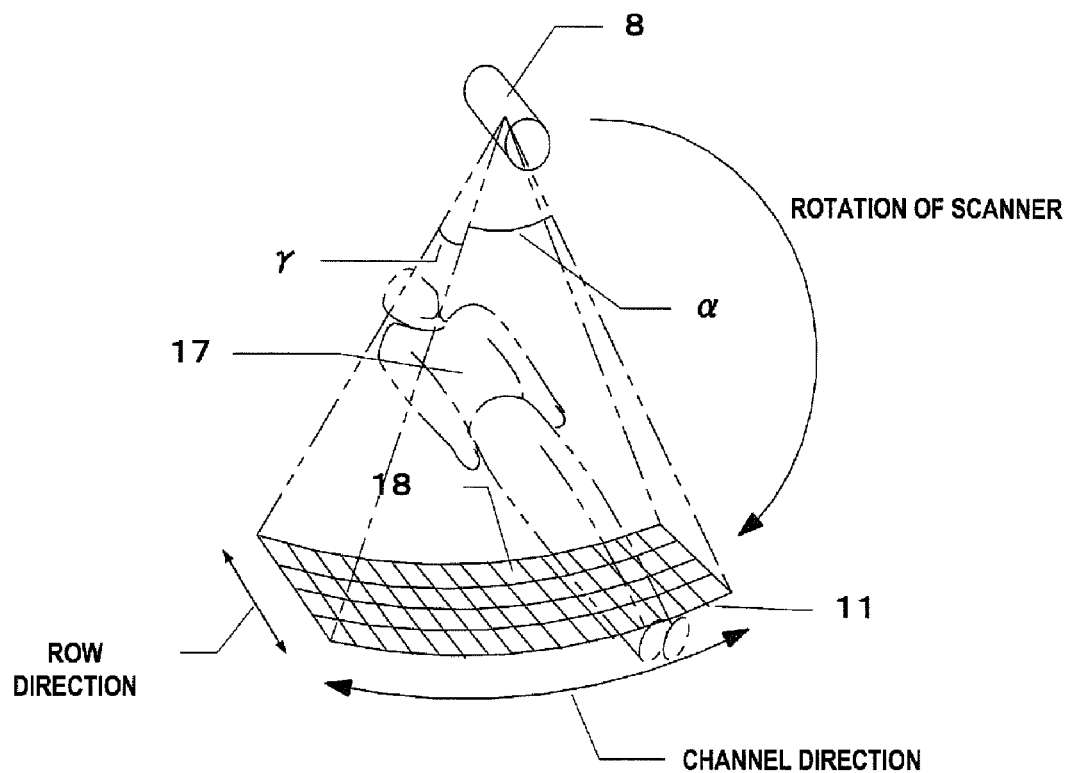
FIG. 3 shows the relation between the configuration of the X-ray detector in the X-ray CT apparatus to which the present invention is applied and X-ray irradiation.
Figure 4:
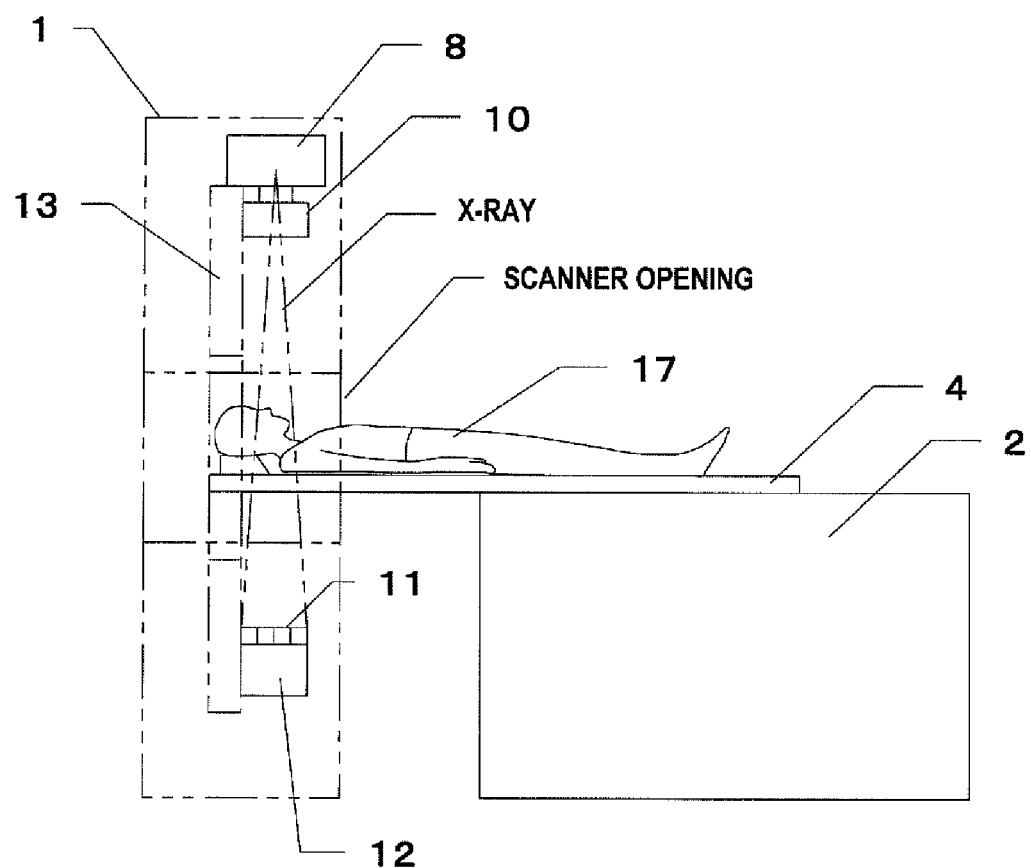
FIG. 4 is a side view showing the relationships among a scanner gantry, a table and an object of the X-ray CT apparatus to which the present invention is applied.

As the positional relationship between X-ray detector 11 and the focal point of X-ray tube 8, ¼ channel off-set detector method is applied for the purpose of improving spatial resolution and reducing fine streak artifacts, and X-ray detector 11 has a plurality of X-ray detection elements 18 that are two-dimensionally arranged in the channel direction and the row direction as shown in FIG. 3.

The X-ray detection elements 18 are configured, for example, by combination of scintillator and photo diode, forming an X-ray incoming surface as a whole being curved in cylindrical form or broken-line form in the channel direction, and channel number "i" is about 1~1000, and the row number "j" is 1~1000.

The spread angle, i.e. fan angle of the cone-beam X-ray in the channel direction to be coincident with the arrangement direction of the channel in X-ray detector 11 is $\alpha$, and the spread angle, i.e. cone angle of the cone-beam X-ray in the row direction being coincident with the arrangement direction of the row in X-ray detector 11 is $\gamma$.

Such configured X-ray detector 11 is connected to data acquisition system 12, and data acquisition system 12 collects the detection data of X-ray detection elements 18 by which X-ray detector 11 is configured.

X-ray controller 7 is configured to control the voltage to be applied between the anode and the cathode of X-ray tube 8 (hereinafter referred to as tube voltage) and the current that flows between the anode and the cathode of X-ray tube 8 (hereinafter referred to as tube current), and to control the tube voltage and tube current detected in tube voltage/tube current detector 27 to be the tube voltage and tube current to correspond to the scan condition which is set by operation device 6 and planned by a scan planning device to be described later (X-ray control means).

The above-described components from X-ray controller 7 to data acquisition system 12 are mounted in rotor plate 13 (scanner rotating means) of scanner gantry 1. Rotor plate 13 rotates around object 17 by the driving force from rotor plate drive device 15 controlled by rotation controller 14, which is transmitted by drive force transmission system 16.

Table 2 comprising movable top board 4 on which object 17 shown in FIG. 1 is placed is configured to carry in/out object 17 to/from X-ray irradiation space (opening) 28 of scanner gantry 1, and control of table vertical movement device 21 and top board movement device 22 by table controller 20 enables adjustment of heights and forward and back movement of top board 4.

Top board position sensor 26 is the position sensor for detecting the position of a top board in the body-axis direction and the vertical direction. The information of top board position sensor 26 is used so that table controller 20 can control top board movement device 22 and table vertical movement device 21 to set a top board to be in a correct position.

Console 3 comprises multi-energy scanning system controller 19 (hereinafter referred to as system controller 19) configured to control the entire multi-energy scanning system of the X-ray CT apparatus related to the present invention, and scanner gantry 1 and table 2 are connected thereto. In other words, system controller 19 controls X-ray controller 7, collimator controller 9, data acquisition system 12, rotation controller 14 in scanner gantry 1, and table controller 20 in table 2.

The data collected by data acquisition system 12 is inputted to image reconstruction device 23 under control of system controller 19.

Image reconstruction device 23 generates scanogram images upon scanogram projecting using scanogram projection data (object fluoroscopic data) collected by data acquisition system 12, and reconstructs CT images upon scanning using projection data of a plurality of views collected by data collection 12.

The scanogram images and CT images generated/reconstructed by image reconstruction device 23, various data and program for actualizing the function of the X-ray CT apparatus, etc. are stored in storage device 24 connected to system controller 19.

Also, display device 5 and operation device 6 are respectively connected to system controller 19.

Display device 5 displays the reconstruction images outputted from image reconstruction device 23 or storage device 24, or a variety of information processed by system controller 19.

operation device 6 is for an operator to input various commands or information to system controller 19, and for interactively operating the present X-ray CT apparatus using display device 5 or operation device 6 (operation means).

To system controller 19, scan planning device 25 for multi-energy scanning (hereinafter referred to as scan planning device 25) which is the relevant part of the present invention is connected (scan planning means). Scan planning device 25 is for determining a scan condition prior to starting scanning using the operation commands inputted by an operator using operating device 6 and the scanogram images read out from storage device 24.

More specifically, the scanogram images read out from storage device 24 are displayed on display device 5, and the operator can set the slice position by specifying the coordinate of CT image reconstruction position (hereinafter referred to as the slice position) using operation device 6 on the displayed scanogram image of the object. The set information of the slice position is to be stored in storage device 24 and to be used for setting X-ray dosage control condition, etc.

The present invention uses such configured X-ray CT apparatus to perform multi-energy scanning capable of acquiring high-quality images through continuous scanning rotation and continuous X-ray irradiation by plural kinds of tube voltages at the same slice position by setting a scan start phase considering the attenuation of X-ray due to an object, setting and transition of the tube voltage/tube current for stabilizing radiation exposure dose and equalizing image noises for the respective tube voltages.

Here, the above-described control of the entire scan is performed under control of system controller 19, and the setting of scan conditions including the setting of scan start phase or tube voltage/tube current and the transition of tube voltage/tube current are executed by scan planning device 25.

In this way, system controller 19 and scan planning device 25 are significant components in the present invention.

Figure 5:
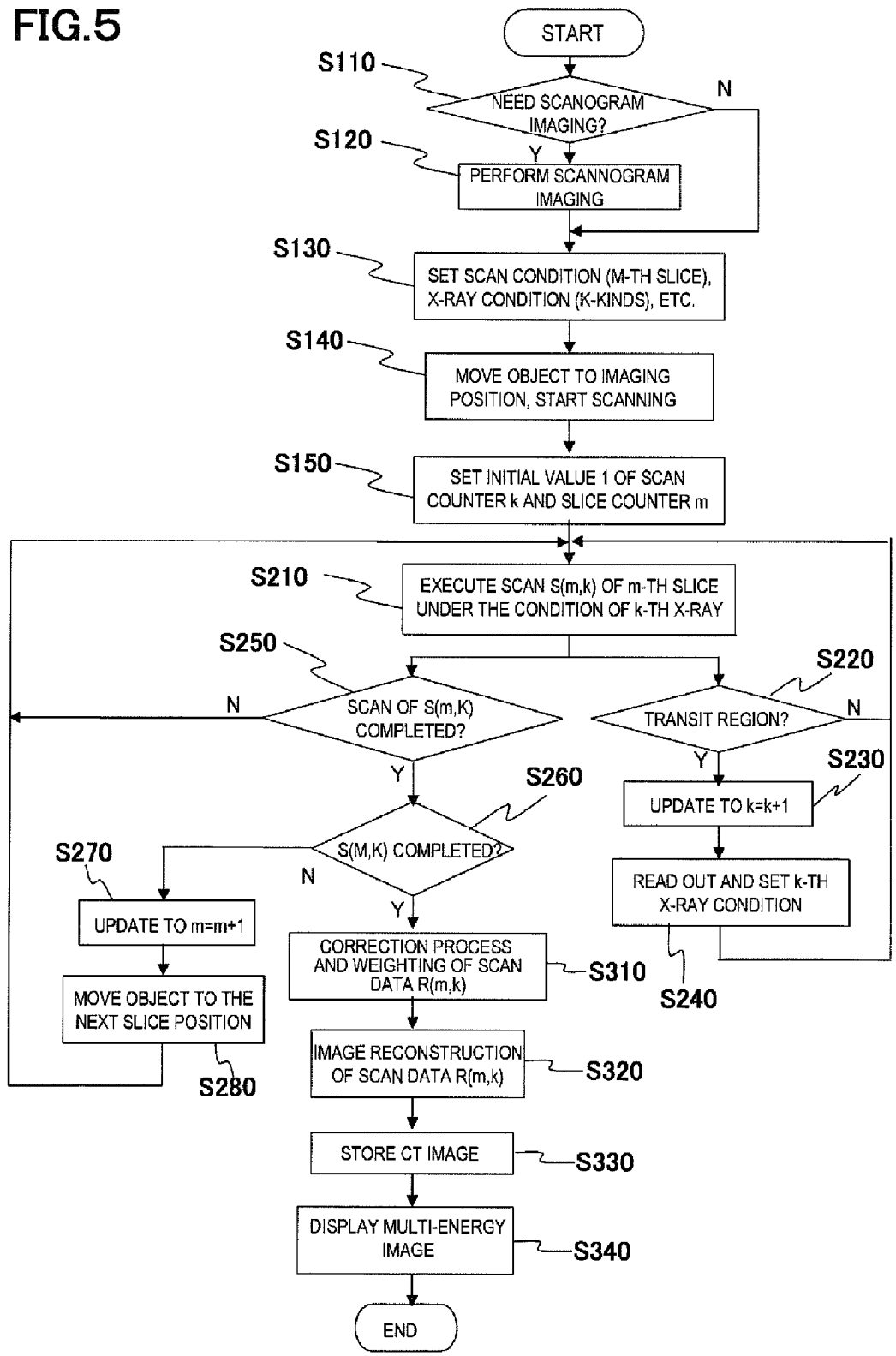
FIG. 5 is an operation flowchart for multi-energy scanning using multi-energy full scan related to the present invention.

FIG. 5 is an operation flowchart of multi-energy full-scan imaging by the present invention. The operation of multi-energy scanning by the present invention will be described using the flowchart.

(1) Setting Necessity of Performing Scanogram Projection (S110)

In multi-energy scanning, it is necessary to set scanning condition and X-ray condition of a plurality of tube voltages/tube currents for scanning with the set scanning condition.

The scanning condition can be set in two ways which are the cases of setting with and without scanogram images. In step S110, the operator inputs the necessity of scanogram projection on the screen of display device 5 using operation device 6. In the case that it is "necessary" to perform scanogram projection, the scanogram projection is to be performed in step S120. Since the scanogram projection to be performed in step S120 is commonly known in various documents, the explanation thereof will be omitted here.

Meanwhile, in the case that it is inputted "unnecessary" to perform scanogram projection by an operator, step S130 is to be carried out.

(2) Setting of Scanning Condition and X-Ray Condition (S130)

(i) Using a Scanogram Image

Scanning condition is set by an operator using a scanogram image generated in step S120. The scanning condition here means the terms and conditions such as the body-axis direction positions of a beginning-CT image/ending-CT image (scanning range or slice number), the interval for creating CT images in the body-axis direction (slice pitch), scan start phase (direction to start scanning an object), scanning velocity (time necessary for an X-ray tube to make one rotation), X-ray collimation condition (slice thickness), X-ray condition (tube voltage, tube current), switching time of tube current (hereinafter referred to as transition time) and changeover timing, the kind of reconstruction filtering function, and visual field size.

As for the tube voltage to be set in step S130, plural kinds (K-kinds) of values are set in order to scan the same cross-sectional plane (slice) of an object with different tube voltages. Since those plural kinds of tube voltage values are different by the conditions such as the object's physical size and constitution, and discriminating target in the examination (discrimination between an organ and contrast medium), the following methods, for example, can be appropriately applied for the setting of a tube voltage in step S130:

{1} By obtaining the tube voltage in advance which corresponds to the above-mentioned conditions on an experimental basis and storing it to the storage device, the tube voltage is to be set in accordance with the object's physical size and constitution, discriminating target in the examination (discrimination of an organ and contrast medium), etc. being inputted by an operator.

{2} By automatically setting the tube voltage from a scanogram image, a plurality of values are to be determined ultimately by a doctor by adding his/her experiences to the previously set value.

As for the tube current also, K-kinds of proper tube currents are set corresponding to the respective K-kinds of tube voltages. These K-kinds of tube current values are calculated and set as below.

While K-times of scanning is to be executed for the same slice in multi-energy scanning, it is desirable that the image noises generated in each scanning be equalized. Considering the equalization of image noises, tube currents $XA_k$ corresponding to K-kinds of tube voltages are to be calculated by equation (1).

$$XA_k = XA_{stAnd} \times f(VX_{stAnd})/P \times f(XV_k)$$ equation (1)

Here, $XA_{stAnd}$: standard tube current of single-energy scanning
$XV_{stAnd}$: standard tube voltage of single-energy scanning
P: number of tube voltages to be applied
f(XV): exposed radiation dose per unit tube current with respect to tube voltage XV When an operator sets $XA_{stAnd}$, the tube currents are automatically calculated with respect to K-kinds of tube voltages by scan planning device 25 using equation (1).

Then the tube voltages automatically set by the device as described above or the tube voltages set by the operator and the tube currents calculated by the above-mentioned equation (1) are stored in storage device 24.

Next, switching time and the timing of switchover of the tube voltages and tube currents will be described. While it is desirable to execute switchover of tube voltage and tube current for collecting scan data at once, it is difficult to execute switchover of tube current instantly compared to tube voltage due to an obstacle caused by thermal inertia of a cathode filament of the X-ray tube which determines the tube current. In other words, it takes more time to switchover (transmission time) the tube current than the tube voltage. Given this factor, in order to reduce the influence of thermal inertia of a filament to the switchover of a tube current and to shorten the switchover-time of the tube current as much as possible, the method is applied in the present invention wherein the value of a tube current is changed in ascending order, the value of a tube voltage is changed in descending order as the scanning proceeds, and the transmission time of the tube voltage is coordinated with the transmission time of the tube current.

The reason for applying this method is that in the case of raising or lowering a tube current from a certain value, the transmission time is shorter to raise the tube current than to lower the current due to the influence of thermal inertia of the cathode filament in an X-ray tube. It also is easier to coordinate the transmission time of the tube voltage to the transmission time of the tube current than vise versa, thereby generating less overshoot in the tube voltage waveform.

While transmission time of a tube current is about 0.05 seconds, transmission TR from tube current $XA_k$ in arbitrary k-th time scanning to tube current $XA_{k+1}$ in the (k+1)-th time scanning for a certain slice can be obtained, to be exact, by calculating the excessive respondence of the relationship between the electric current being passed to the filament by an X-ray tube filament heating circuit (filament current) and the temperature of the filament and the relationship between the temperature of the filament and the tube current. It is desirable to store the previously mentioned calculation program in storage device 24 in advance, so that scan planning device 25 can execute the calculation using the stored program upon completion of the K-kinds of combinations of the tube voltage and the tube current.

Such obtained transmission time TR is stored in storage device 24, and read out when an operator inputs a command to start scanning to be used for the switch-over control of a tube voltage and a tube current. Transmission time TR is arranged between one rotation scanning by a certain X-ray energy to one rotation scanning by the next X-ray energy. It means that TR/2 is arranged right before the end of one rotation scanning by certain X-ray energy, and the remaining TR/2 is arranged right after the end of one rotation scanning by the next X-ray energy.

Other than measuring TR or TR/2 as time, they can be measured as the angle based on a scanning time or the view number based on the measured view number of one scanning. An angle detection switch or a counter can be used according to the method of measurement.

Also, since tube current value $XA_{tr}$ at time "tr" after starting tube current switch-over can be obtained by the above-described calculation, by obtaining tube voltage $XV_{tr}$ during the transition period of the tube current using the following expression (2), it can be controlled so that the switchover of both tube voltage and tube current can complete at the same time after passage of transit time TR of the tube current and tube voltage.

$$XV_{tr} = f^{-1}(XA_{stAnd} \times (XV_{stAnd})/(P \times XA_{tr}))$$ expression (2)

Here, $XA_{tr}$ is the function of time, and $XV_{tr}$ is also the function of time. Also, function $f(XV_{stAnd})$ is the function used in expression (1), and function $f^{-1}$ is the inverse function of function $f(XV)$. Further, $XA_{tr}$ is the tube current during the transition period, equal to $XA_k$ upon starting the transition period and is equal to $XA_{k+1}$ after completion of the transition period.

$XV_{tr}$ to be calculated by the above-mentioned expression (2) may be calculated by scan planning device 25 in advance before starting the scanning and stored in storage device 24, or may be calculated along with the scanning process.

$XV_{tr}$ is to be used as a tube voltage control signal when the scanning is in the transition period.

Figure 6:
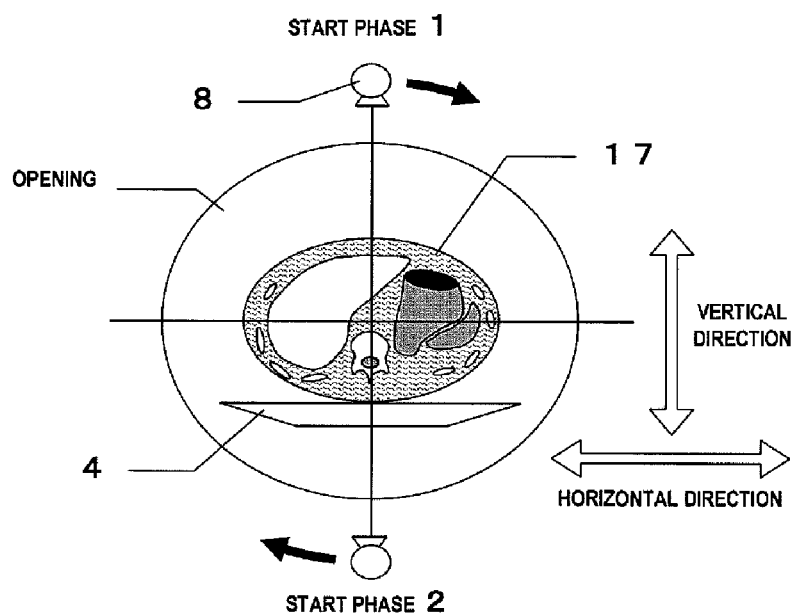
FIG. 6 shows a preferable scan start phase.
Figure 6:
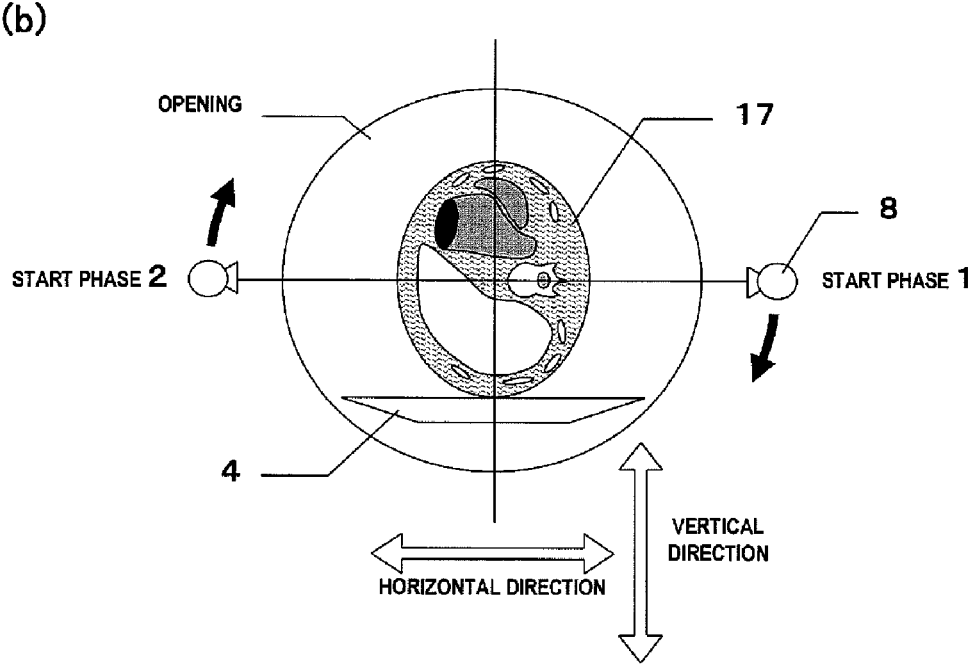

Next, the scanning start phase to be set in step S130 will be described. The scanning start phase which is the position of the X-ray tube at which the measurement of X-ray transmission data is started is to be set at the angle (position) wherein the X-ray attenuation attributed to an object reaches the minimum value. For example, in the case that the X-ray attenuation in the vertical direction reaches the minimum value (when object is in the face-up position), the scanning start phase is to be set in scanning start phase 1 (at the position wherein an X-ray tube is right above the object at 0° angle) or in scanning start phase 2 (at the position wherein the X-ray tube is right under the object at 180° angle) as shown in FIG. 6(*a*). Also, in the case that the X-ray attenuation in the horizontal direction reaches the minimum value (in the case that the object is in the side-lying position), the scanning start phase is to be set in scanning start phase 1 (the position wherein the X-ray tube is at the front face of the object at 90° angle) or in scanning start phase 2 (the position wherein the X-ray tube is immediately posterior to the object at 270° angle) as shown in FIG. 6(*b*).

As for the setting of the scanning start phase, the method can be applied wherein scan planning device 25 estimates the shape of cross section of the object from scanogram data, calculates the direction in which the X-ray attenuation attributed to the object is minimum and automatically sets the scanning start phase, or the method wherein an operator manually inputs the setting. The method for estimating the cross section of the object from scanogram data is disclosed in JP-A-2001-276040.

The set scanning start phase is stored in storage device 24, and read out by system controller 19 to be used for scanning control when the operator inputs the command to start scanning as mentioned above.

In the present X-ray CT apparatus, multi-energy scanning is performed while changing the X-ray conditions between the scans without interrupting the scan rotation. For this reason, since the measurement data during the transition period of X-ray conditions does not correlate with the measurement data during other scanning periods, if the measurement data of transition period is used for image reconstruction the way it is, a negative influence such as generation of artifacts may be a concern. Given this factor, in the present invention, the proportion for using the measurement data of transition period in image reconstruction is reduced, and the reduced portion is compensated by adding large weight on the opposing data. For this purpose, the weighting of measurement data is to be carried out.

Figure 7:
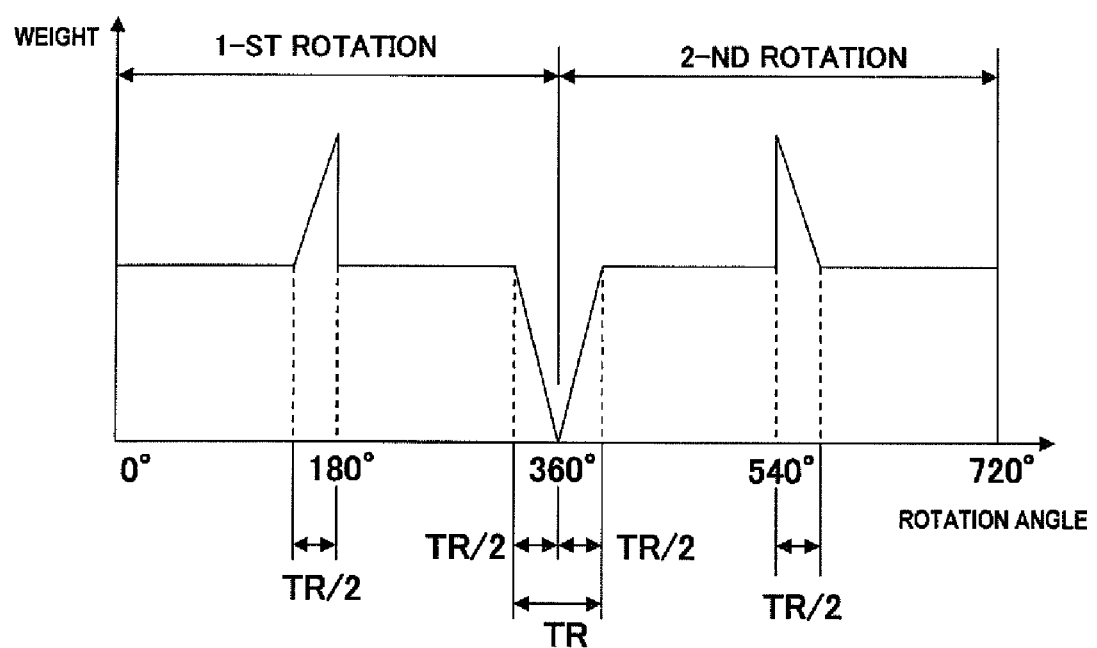
FIG. 7 shows a view weight in the case of full scanning.

FIG. 7 illustrates the concept of the above-mentioned weighting of the measurement data. As shown in FIG. 7, the weighting method of the measurement data in the present invention is to compensate the measurement data of the respective channels of the detector which configures the view data within the range of transition period TR/2 right before the completion of a first rotation (360° by the opposing data which is measured before the transition period TR/2 (the weighting in the central channel of the detector is illustrated in FIG. 7). It is preferable to vary the weight value of transition period TR/2, for example in the range from 1 to 0, and to vary the weight value to be added to the opposing data, for example in the range from 1 to 2. Also, weighting of the measurement data in the second rotation is to be executed in the same manner.

The above-described weighting data is calculated and set in scan planning device 25 after transition period TR is calculated, and stored in storage device 24 to be used for image reconstruction.

Though the above-described weighting method has slight disadvantage in the point of image noise compared to the method to carry out weighting of 1 scan with exactly the same X-ray condition, it has an advantage in saving time for measurement since there is no interruption of scanning. Also, while this method requires longer time for measurement compared to the half-scan reconstruction method, it excels in the point of image noise.

(ii) Without Using a Scanogram Image

When an operator selects "No" for scanogram projection in step S110, step S130 is to be carried out without execution of scanogram projection. While the above-mentioned scanning condition and X-ray condition are the same as previously mentioned step S130, the position of the starting-CT image and the ending-CT image are set by a light localizer which is installed in gantry 1.

The scanning condition and X-ray condition being set in the above-mentioned step S130 are stored in storage device 24 by scan planning device 25.

(3) Moving an Object and Starting-Up Scanning (S140)

When the setting of scanning condition and X-ray condition is completed, the operator inputs the command to console 3 to move the object to an scanning position. Then system controller 19 outputs the command to table controller 20 to move object 17 to the scanning position (scanning position of the starting-CT image). In this manner, top-board movement device 22 is controlled, and the scanning position of starting-CT image of object 17, i.e. the position of slice No. 1 is moved to the surface of revolution of X-ray tube 8 and detector 11.

(4) Start of Scanning, and Setting of Initial Values for Scan Counter k and Slice Counter m (S150)

After moving the object, the operator inputs the command to start scanning to console 3. Then system controller 19 respectively sets initial values "k=1" and "m=1" to scan counter k and slice counter m, and outputs an scanning start signal to scanner gantry 1. Scan counter k is for counting the scan number with respect to the same slice, and slice counter m is for counting what number of slice is being scanned. These scan counter k and slice counter m are mounted in system controller 19 as a counter circuit.

In gantry 1 where the scanning start signal is received, scanner rotor plate 13 on which X-ray tube 8 and detector 11 are mounted is rotated by rotor plate driving device 15.

Meanwhile, corresponding to initial value "k=1" being set in scan counter K, the first X-ray condition (k=1) out of K-kinds of X-ray conditions of multi-energy scanning is read out from storage device 24, and outputted to X-ray controller 7 as a setting signal of tube voltage and tube current. In this manner, the tube voltage and the tube current are set by X-ray controller 7.

(5) Execution of Xcan S(m,k) (S210)

When the detector for detecting the rotation of scanner rotor place 13 detects that X-ray tube 8 had arrived to the scan starting phase, the set tube voltage and tube current are applied to X-ray tube 8, and CT scan S(1,1) is to be started with respect to the first slice (m=1) with the X-ray energy of k=1. Then along with the start of scanning, the X-ray being irradiated from X-ray tube 8 and transmitted through object 17 is detected in detector 11, made into detection data of the respective views in data acquisition system 12 and stored in storage device 24.

During execution of scanning, the values of the tube voltage and the tube current detected by tube voltage/tube current detection device 27 are compared to the set values of the tube voltage and the tube current, and are adjusted under feedback control to be the set values.

(6) Change of X-Ray Condition (X-Ray Energy)

(i) Determination Whether being in the Transition Region or not (S220)

The progress of CT scan is monitored by system controller 19, and determines whether X-ray tube 8 has reached the TR/2 region (transition region) before completion of the first rotation from scanning start phase.

(ii) Update of Scan Counter k (S230)

If it is determined that X-ray tube 8 has reached the transition region, system controller 19 adds 1 to scan counter k.

(iii) Update of X-Ray Condition (S240)

Figure 8:
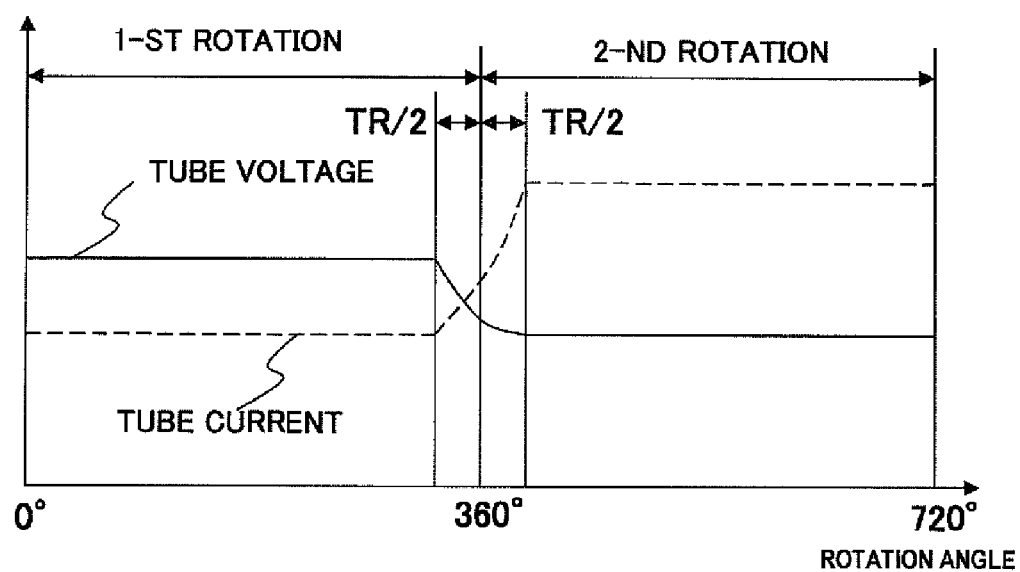
FIG. 8 is an explanatory diagram of preferable transition of a tube voltage and a tube current.

When scan counter k is updated, system controller 19 reads out the X-ray condition of k=2 from storage device 24, and outputs it to scan planning device 25. Then scan planning device 25 outputs the tube voltage and tube current to be set constantly. System controller 19 then outputs the tube voltage/tube current setting signals to X-ray controller 7 according to the set values. In this manner, X-ray condition is sequentially updated as shown in FIG. 8.

(7) Determination of the Completion of Scan S(m,K) (S250)

Next, system controller 19 determines whether or not the scanning for the first slice is completed. This determination is made when the value of scan counter k and the detection signal denoting that the first rotation of scanner rotor plate 13 is completed or the measurement view number reach the predetermined values. In the explanatory example above, it is determined that the scanning for m=1, k=1 is completed by the completion signal of the first rotation of scanner rotor plate 13.

Scan S(1,2) of m=1, k=2 is to be continuously executed.

Scan S(1,2) is started from the time that X-ray tube 8 passes through the scanning start phase. The X-ray condition is in changing process when scan S(1,2) is started, and changes to k=2 when X-ray tube proceeds from the scanning start phase for the portion of TR/2.

The above-described steps S210-S250 are executed for scan S(1,2) and also with subsequent scans S(1,K). When scanning of the set K-kinds of X-ray conditions are executed, scan counter k would not be updated anymore, and scan S(1,K) for the first slice m=1 is completed. The X-ray irradiation is then discontinued. It is desirable to set the rotation of scanner rotor plate 13 so that rotation is continued even when the X-ray irradiation is discontinued. By doing so, upon scanning the next slice, it is possible to omit the accelerating step to bring back the rotation velocity of scanner rotor plate 13 to steady-state velocity.

(8) Update of Slice Counter m (S270)

When scan S(1,K) is completed, system controller 19 adds 1 to slice counter m to make m=2. At this time, system controller 19 returns scan counter k back to initial value k=1, and transmits the signal to set the X-ray condition of k=1 to X-ray controller 7.

(9) Change of Slice Position (S280)

Along with execution of step S270, system controller 19 issues a command to table controller 20 to move a top board for the portion of 1 slice pitch. By doing so, top-board moving device 22 moves the top board for the portion of 1 slice pitch, and the second slice position of object 17 is moved to the position of revolution surface of X-ray tube 8 and detector 11.

When the movement of object 17 is completed, execution of scan S(2,1) is to be started in the timing that X-ray tube 8 arrives in the scanning start phase.

Thereafter, multi-energy scan is executed for the second slice in the same manner as for the first slice. Further, multi-energy scan is executed for the entire set slice positions.

(10) Preprocessing of Image Reconstruction (i) Compensation and Weighting of Scan Data R(m,k) (S310)

When scan S(m,k) is completed, system controller 19 issues a command to image reconstruction device 23 to execute image reconstruction. The image reconstruction device 23 reads out scan data of R(m,k) from storage device 24, and performs compensation process on projection data (view data) which configures each portion of scan data. The compensation process to be executed here includes, for example:

{1} Offset compensation (of the detector) which subtracts the detector output of the time when no X-ray is irradiated from the measurement data;

{2} Sensitivity fluctuation compensation (of the detector) which compensates the sensitivity fluctuation among the elements of the X-ray detector; and {3} log conversion process which converts the measurement data after the above-mentioned compensation into the projection data proportional to the X-ray absorption coefficient integral value along the X-ray transmission path.

After these compensation process are completed, image reconstruction device 23 executes the weighting of scan data as shown in FIG. 7. The weighting is to be executed, as an example, as follows:

{11} Read out the weighting data of FIG. 7 from storage device 24;

{12} Multiply the view data within the X-ray condition transition period in each scan data R(m,k) by the relevant weight (<1); and {13} Read out the opposing data of the respective channels of the view data by which the above-mentioned weight is multiplied, and multiply the readout opposing data by the weight (>1) which is in the period of TR/2 right before 180° in FIG. 7 and is on the opposite angle with respect to the multiplied weight data.

By executing the weighting of the above-described {11}~{13}, the projection data for image reconstruction of the respective scan data R(m,k) is generated.

(ii) Image Reconstruction (S320)

Image reconstruction device 23 executes back projection after executing the reconstruction filtering process for deblurring with respect each scan data R(m,k) that are performed with the weighting process.

In this manner, K-kinds of CT images by high-energy X-ray and low-energy X-ray can be acquired for M-number of the respective slices. While it is described in the present embodiment to execute the above-described steps S310 and S320 after completing the entire scan S(m,k), the present invention does not have to be limited thereto, and the steps S310 and S320 may be executed upon completion of scanning by each X-ray energy or upon completion of multi-energy scanning for the respective slices.

(11) Storage of CT Images (S330)

The obtained images by multi-energy scanning are stored in storage device 24.

(12) Display of Images by Multi-Energy Scanning (S340)

The images by multi-energy scanning stored in storage device 24 are displayed on a display screen of display device 5 along with the supplementary information such as slice position or number and X-ray conditions, in the form desired by an operator, to be used by a doctor for diagnosis.

Conceivable display patterns of multi-energy scanning images are such as the pattern to juxtapose CT images scanned using different X-ray energies on the display screen of display 5, the pattern to display the difference image obtained by calculating difference of CT images scanned using different X-ray energies, or the pattern to display the multi-energy scanning images of the respective slices performed with 3-dimensional reconstruction on every X-ray energy.

Display of such multi-energy scanning images enables the discrimination between the X-ray contrast medium injected into the object and bones.

While the first embodiment of the present invention is described above, no limitations are intended thereto, and the embodiment may be altered or modified.

Second embodiment of the present invention will be described below. The difference from the first embodiment is that while the CT scanning using the first X-ray energy and the CT scanning using the second X-ray energy are executed by one rotation scan (full scan) in the first embodiment, they are to be executed in the second embodiment continuously by half scan which is less than one rotation and preferably with scan angle of (½ rotation+fan angle of X-ray beam≈240°.

In order to execute the above-mentioned process, the following changes need to be made in the previously described first embodiment:

(a) Change the scan angle of 1 scan to α (<360°, or the measurement view number of 1 scan to the one to correspond to half-scan. Corresponding to this change, for example, change the position of an angle detecting sensor for 1 scan or the maximum value of the counter of measurement view per one scan.

(b) Change the scanning start phase. Corresponding to this change, for example, when the scanning start phase of the first scan is set as 0°, the scanning start phase for the second scan is set as α.

Figure 9:
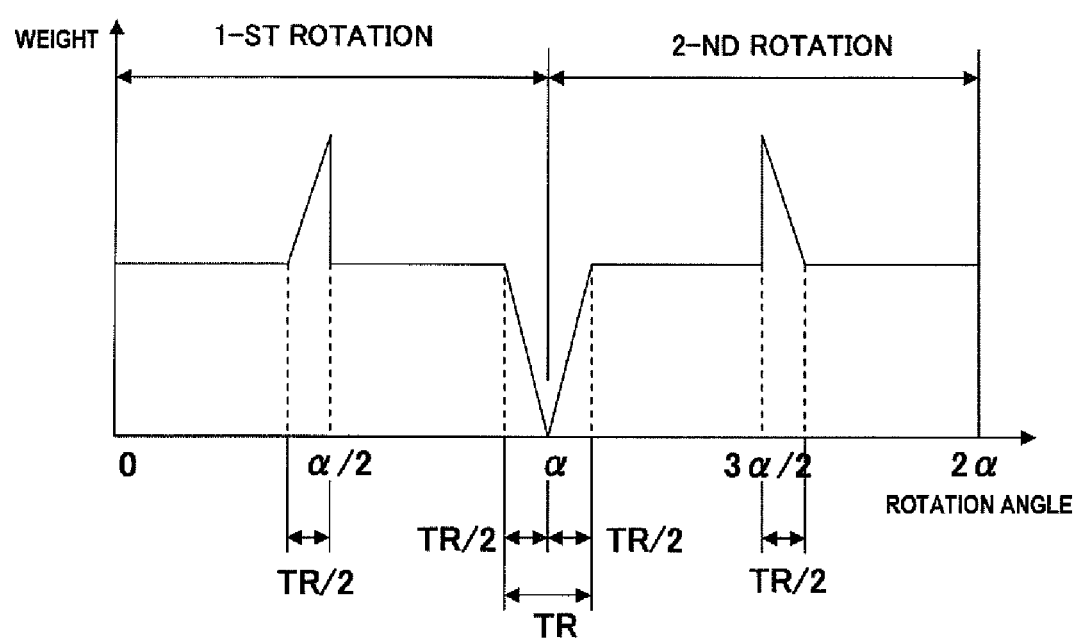
FIG. 9 shows a view weight in the case of half-scanning.

(c) Change the weighting data shown in FIG. 7 to the weighting data shown in FIG. 9.

(d) Re-set the opposing data of the measurement view in the transition region of the tube voltage/tube current.

The re-setting can be executed by carrying out geometric calculation using a computer. It can be easily understood from geometric view that when the fan angle of an X-ray beam is assumed as 60°, the opposing data of the respective view data in the transition period defined in the present invention can be obtained in the half scan of 180° (½ rotation)+60°-240°.

(e) Store the image reconstruction software by the half scan in the storage device.

By changing hardware/software described in the above (a)~(e) and executing multi-energy CT scanning according to the flowchart shown in FIG. 5, it is possible to obtain multi-energy CT images of the object at higher speed.

As mentioned above, by comprising only a pair of an X-ray tube and a non-multilayered detector, the X-ray CT apparatus to which the multi-energy scanning function provided by the present invention is applied is capable of achieving multi-energy scanning having the sufficient difference of X-ray effective energies by switching of tube voltages and obtaining high-quality images with less image noise or streak artifacts than half scan by using full scan in the respective tube voltages, without using an expensive X-ray CT apparatus to which a method such as multi-source/multilayered-detector method or multi-layered detector method is applied.

While the present invention has been described using the above-mentioned embodiments, the present invention is not limited thereto and various changes and alterations may be made within the scope of multi-energy full-scan method which executes scanning of the same slice position by different X-ray conditions using a scanner comprising a pair of X-ray source and a non-multilayered detector.

The invention claimed is:

1. An X-ray CT apparatus including: a pair of an X-ray tube and a detector configured to irradiate X-rays to an object to be examined and to detect the X-rays transmitted through the object; scanner rotation means to which the pair of the X-ray tube and the detector is mounted, configured to rotate around the object; multi-energy scanning planning means configured to execute CT scanning of the same slice position of the object with the X-rays having different X-ray energies; and X-ray control means configured to control the irradiation of the X-rays having different energies from the X-ray tube, characterized in further comprising: means configured to continuously executing a first CT scanning using a first X-ray energy and a second CT scanning using a second X-ray energy without interrupting the CT scanning; means configured to transit the X-ray energy irradiated from the X-ray tube from the first X-ray energy to the second X-ray energy during transition period including the ending of the first CT scanning and the beginning of the second CT scanning; and means configured to execute image reconstruction by compensating the scan data of the transition period using the scan data of the remaining period.

2. The X-ray CT apparatus according to claim 1, wherein the first CT scanning using the first X-ray energy and the second CT scanning using the second X-ray energy are executed as full scan of 1 rotation.

3. The X-ray CT apparatus according to claim 1, wherein the first CT scanning using the first X-ray energy and the second CT scanning using the second X-ray energy are executed as a half scan.

4. The X-ray CT apparatus according to claim 1, wherein multi-energy scanning planning means comprises: scanning start phase setting means configured to set a scanning start phase which is the scanning start position of the X-ray tube at an angle wherein the X-ray attenuation due to an object is minimum; X-ray condition setting means configured to set the X-ray condition wherein the radiation dose ratio of the object in the first CT scanning and the second CT scanning are to be the same; and X-ray condition transition means configured to set the transition state of the X-ray condition in the first CT scanning and the second CT scanning.

5. The X-ray CT apparatus according to claim 4, wherein the scanning start phase setting means comprises scanning start phase calculation means configured to estimate the cross-sectional shape of the object from a scanogram image of the object so as to obtain the phase having the minimum X-ray attenuation attributed to the object.

6. The X-ray CT apparatus according to claim 1, wherein the image reconstruction means executes weighting on scan data during the transition period and opposing data of the scan data during the transition period so as to minimize the influence of the scan data during the transition period to the image reconstruction.

7. The X-ray CT apparatus according to claim 4, wherein the X-ray condition setting means comprises tube current calculation means configured to calculate the tube current value wherein the image noises of the image acquired for every set tube voltage are to be substantively the same.

8. The X-ray CT apparatus according to claim 7, wherein the X-ray condition setting means sets the set tube voltages in order of scanning and in descending sequence, and the obtained tube currents in order of scanning and in ascending sequence.

9. The X-ray CT apparatus according to claim 4, wherein the X-ray condition transition means obtains the transition period of a tube current, and executes the transition of a tube voltage in time along with the transition of the tube current.

* * * * *